(12) United States Patent
Pernodet et al.

(10) Patent No.: US 10,010,492 B2
(45) Date of Patent: Jul. 3, 2018

(54) METHODS AND COMPOSITIONS FOR TREATING SKIN TO RESOLVE INFLAMMATION AND SCREENING FOR ACTIVES THAT STIMULATE PRO-RESOLUTION PATHWAYS

(71) Applicant: ELC Management LLC, Melville, NY (US)

(72) Inventors: Nadine A. Pernodet, Huntington Station, NY (US); Donald F. Collins, Plainview, NY (US); Fatemeh Mohammadi, Hauppauge, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 15/590,390

(22) Filed: May 9, 2017

(65) Prior Publication Data

US 2017/0319451 A1 Nov. 9, 2017

Related U.S. Application Data

(62) Division of application No. 15/054,815, filed on Feb. 26, 2016, now Pat. No. 9,682,034.

(60) Provisional application No. 62/130,644, filed on Mar. 10, 2015.

(51) Int. Cl.
| | | |
|---|---|---|
| *A61K 8/365* | (2006.01) | |
| *A61Q 5/00* | (2006.01) | |
| *A61Q 19/00* | (2006.01) | |
| *A61Q 3/00* | (2006.01) | |
| *A61K 8/368* | (2006.01) | |
| *A61K 8/99* | (2017.01) | |
| *A61K 8/06* | (2006.01) | |
| *G01N 33/50* | (2006.01) | |

(52) U.S. Cl.
CPC ............... *A61K 8/365* (2013.01); *A61K 8/06* (2013.01); *A61K 8/062* (2013.01); *A61K 8/368* (2013.01); *A61K 8/99* (2013.01); *A61Q 3/00* (2013.01); *A61Q 5/00* (2013.01); *A61Q 19/00* (2013.01); *G01N 33/5038* (2013.01); *G01N 33/5044* (2013.01); *G01N 2800/7095* (2013.01)

(58) Field of Classification Search
None
See application file for complete search history.

(56) References Cited

U.S. PATENT DOCUMENTS

| | | | |
|---|---|---|---|
| 6,270,780 B1 * | 8/2001 | Carson | A61K 8/347 424/401 |
| 2008/0161275 A1 * | 7/2008 | Gjorstrup | A61K 31/202 514/164 |
| 2009/0280150 A1 * | 11/2009 | Kamen | A45D 34/04 424/401 |

* cited by examiner

*Primary Examiner* — Robert A Wax
*Assistant Examiner* — Quanglong N Truong
(74) *Attorney, Agent, or Firm* — Julie M. Blackburn

(57) ABSTRACT

Compositions and methods for treating inflamed skin with Pro-Resolution Pathway Stimulators that may be Inflammatory Metabolite Inhibitors, Pro-Resolving Activators, or combinations thereof, and a method for screening active ingredients for activity as Pro-Resolution Pathway Stimulators for incorporation into topical cosmetic products.

16 Claims, 7 Drawing Sheets

FIGURE 1A

| Active | Dose (in µg/ml or %) | Mean | SEM | % of control |
|---|---|---|---|---|
| Salicylic Acid | Ctrl DMSO | 447895 | 131 | 100 |
| | 0.0000033 | 42491 | 448 | 89 |
| | 0.000033 | 39012 | 762 | 81 |
| | 0.00033 | 39113 | 721 | 82 |
| | 0.0033 | 39662 | 526 | 83 |
| | 0.033 | 39351 | 683 | 82 |
| | 0.33 | 38853 | 365 | 81 |
| | 3.3 | 38931 | 825 | 81 |
| | 33 | 41543 | 1339 | 87 |
| | | | | |
| *Poria cocos* | Ctrl DMSO | 447895 | 131 | 100 |
| | 0.00001 | 44003 | 1589 | 92 |
| | 0.0001 | 43262 | 1589 | 90 |
| | 0.001 | 42780 | 2176 | 89 |
| | 0.01 | 42311 | 2272 | 88 |
| | 0.1 | 40833 | 2698 | 85 |
| | 1 | 41918 | 2398 | 88 |
| | 10 | 42773 | 1838 | 89 |
| | 100 | 47461 | 1235 | 99 |

FIGURE 1B

| Resveratrol salicylate | Ctrl DMSO | 48083 | 137 | 100 |
|---|---|---|---|---|
| | 0.0000043 | 42944 | 1058 | 89 |
| | 0.000043 | 42004 | 620 | 87 |
| | 0.00043 | 41068 | 1122 | 85 |
| | 0.0043 | 41017 | 879 | 85 |
| | 0.043 | 40675 | 669 | 85 |
| | 0.43 | 39655 | 726 | 82 |
| | 4.3 | 39994 | 1603 | 83 |
| | 43 | 40900 | 1832 | 85 |

| Resveratrol | Ctrl DMSO | 48083 | 137 | 100 |
|---|---|---|---|---|
| | 0.00001 | 44058 | 1635 | 92 |
| | 0.0001 | 47019 | 1460 | 98 |
| | 0.001 | 45399 | 2191 | 94 |
| | 0.01 | 43251 | 1524 | 90 |
| | 0.1 | 42921 | 2222 | 89 |
| | 1 | 42858 | 2281 | 89 |
| | 10 | 41702 | 2272 | 87 |
| | 100 | 27904 | 1094 | 58 |

| Figure 1C | | | | |
|---|---|---|---|---|
| *Dongbaek* (Tsubuki oil) | Ctrl | 46102 | 380 | 100 |
| | 0.00000001% | 43340 | 1146 | 94 |
| | 0.0000001% | 41560 | 429 | 90 |
| | 0.000001% | 40299 | 1033 | 87 |
| | 0.00001% | 39515 | 1556 | 86 |
| | 0.0001% | 39093 | 674 | 85 |
| | 0.001% | 39342 | 1145 | 85 |
| | 0.01% | 38279 | 1126 | 83 |
| | 0.1% | 37427 | 1523 | 81 |
| | | | | |
| *Camelina sativa* seed oil | Ctrl | 46102 | 380 | 100 |
| | 0.00000001% | 43651 | 1541 | 95 |
| | 0.0000001% | 43291 | 1542 | 94 |
| | 0.000001% | 42364 | 1827 | 92 |
| | 0.00001% | 41838 | 1607 | 91 |
| | 0.0001% | 41367 | 2402 | 90 |
| | 0.001% | 41879 | 2350 | 91 |
| | 0.01% | 41058 | 2958 | 89 |
| | 0.1% | 41744 | 1958 | 91 |

| FIGURE 1D | | | | |
|---|---|---|---|---|
| *Kukui* nut oil | Ctrl | 44820 | 627 | 100 |
| | 0.00000001% | 42202 | 962 | 94 |
| | 0.0000001% | 39924 | 868 | 89 |
| | 0.000001% | 39037 | 1177 | 87 |
| | 0.00001% | 38556 | 1254 | 86 |
| | 0.0001% | 38265 | 700 | 85 |
| | 0.001% | 37403 | 1137 | 83 |
| | 0.01% | 37863 | 965 | 84 |
| | 0.1% | 38714 | 665 | 86 |
| *Perilla ocymoides* extract | Ctrl | 44820 | 627 | 100 |
| | 0.00000001% | 42741 | 1667 | 95 |
| | 0.0000001% | 41784 | 2055 | 93 |
| | 0.000001% | 41334 | 2013 | 92 |
| | 0.00001% | 40765 | 2520 | 91 |
| | 0.0001% | 40983 | 2181 | 91 |
| | 0.001% | 39951 | 2087 | 89 |
| | 0.01% | 38522 | 1831 | 86 |
| | 0.1% | 38181 | 681 | 85 |

FIGURE 2

| Active | Dose | Inflammatory Metabolites/Markers | | | Pro-Resolving Lipid Mediator Markers | | | | |
|---|---|---|---|---|---|---|---|---|---|
| | | PGE2 | LTB4 | 5-HETE | 15-HETE | 12-HETE | 14-HDOHE | 18-HEPE | 17-HDOHE |
| CTRL (untreated cells) | -- | -- | -- | -- | -- | -- | -- | -- | -- |
| Salicylic Acid | 33 µg/ml | -19 | -17 | -10 | -27 | 6 | -1 | 0 | 0 |
| | 3.3 | -28 | -12 | -18 | -20 | 11 | 1 | 0 | 0 |
| | 0.33 | -19 | -1 | -9 | -15 | 21 | 6 | 0 | 0 |
| Resveratrol | 10 µg/ml | -96 | 14 | -24 | -48 | 40 | -2 | 0 | 0 |
| | 1 | -44 | -4 | -11 | -21 | 8 | -3 | 0 | 0 |
| | 0.1 | -28 | -8 | -9 | -18 | 5 | -16 | 0 | 0 |
| Resveratrol salicylate | 43 µg/ml | -57 | -100 | -100 | -20 | 23 | 34 | 0 | 0 |
| | 4.3 | 1 | -82 | -82 | -11 | 8 | 7 | 0 | 0 |
| | 0.43 | -37 | -26 | -24 | -23 | 20 | 1 | 0 | 0 |
| Poria cocos | 100 µg/ml | 8 | -100 | -97 | -45 | 27 | -63 | 0 | 0 |
| | 10 | -16 | -27 | -33 | -7 | 13 | -18 | 0 | 0 |
| | 1 | -4 | 9 | 8 | -14 | 7 | 2 | 0 | 0 |

FIGURE 2 (cont'd)

| Active | Dose | Inflammatory Metabolites/Markers | | | Pro-Resolving Lipid Mediator Markers | | | | |
|---|---|---|---|---|---|---|---|---|---|
| | | PGE2 | LTB4 | 5-HETE | 15-HETE | 12-HETE | 14-HDOHE | 18-HEPE | 17-HDOHE |
| Dongbaek (Tsubaki) oil | 0.1% | 22 | 0 | -19 | -5 | 13 | 20 | 0 | 0 |
| | 0.01 | -25 | -12 | -23 | -17 | 7 | 4 | 0 | 0 |
| | 0.001 | -40 | -18 | -23 | -25 | 8 | -4 | 0 | 0 |
| | | | | | | | | | |
| Camellina sativa | 0.1% | -2 | 2 | -24 | 18 | 10 | 13 | 0 | 0 |
| | 0.01 | -13 | -20 | -26 | -8 | -3 | -3 | 0 | 0 |
| | 0.001 | -5 | -20 | -25 | -18 | -9 | -13 | 0 | 0 |
| | | | | | | | | | |
| Kukui nut oil | 0.1% | 59 | 6 | -20 | 22 | 2 | -2 | 0 | 0 |
| | 0.01 | -5 | -22 | -27 | -11 | 3 | -6 | 0 | 0 |
| | 0.001 | -20 | -27 | -34 | -17 | -4 | -11 | 0 | 0 |
| | | | | | | | | | |
| Perilla ocymoides | 0.1% | 4 | -5 | -30 | 8 | 17 | 8 | 0 | 0 |
| | 0.01 | -19 | -24 | -27 | -34 | -4 | -8 | 0 | 0 |
| | 0.001 | -13 | -17 | -13 | -19 | -5 | -16 | 0 | 0 |
| Bifida ferment lysate | 10% | 0 | -77 | -30 | 321 | 115 | 110 | | |
| Lactobacillus | 5% | 0 | -100 | -100 | 310 | -78 | -13 | | |
| Dhatelo oil | 0.1% | 37 | 10 | 16 | 67 | 10 | 6 | | |

FIGURE 3

| Active | Concentration | Aggregate % decrease* in cell concentration of Inflammatory Metabolites or Inflammatory Metabolite Markers | Aggregate % increase in cell concentration of Pro-Resolving Lipid Mediators |
|---|---|---|---|
| Untreated cells | -- | -- | -- |
| Cells treated with inflammatory precipitating condition (PMA/A23187) | 1 µg/ml | -253 | 139 |
| Salicylic acid | 33 µg/ml | 46 | 5 |
| | 3.3 µg/ml | 58 | -8 |
| | 0.33 µg/ml | 44 | 27 |
| Resveratrol | 10 µg/ml | 154 | -10 |
| | 1 µg/ml | 80 | -16 |
| Resveratrol salicylate | 43 µg/ml | 257 | 37 |
| | 4.3 µg/ml | 163 | -16 |
| | 0.43 µg/ml | 87 | -2 |
| *Poria cocos* extract | 100 µg/ml | 189 | -85 |
| | 10 ug/ml | 76 | -22 |
| | 1 ug/ml | -13 | -6 |
| *Dongbaek* (Tsubaki) oil | 0.1% | -3 | 28 |
| | 0.01% | 54 | -4 |
| | 0.001% | 81 | -21 |
| *Camellina sativa* extract | 0.1% | -45 | -40 |
| | 0.01% | 59 | -14 |
| | 0.001% | 50 | -40 |
| *Aleurites moluccana* (Kukui) seed oil | 0.1% | -45 | 22 |
| | 0.01% | 54 | -46 |
| | 0.001% | 81 | -32 |
| *Perilla ocymoides* extract | 0.1% | 31 | 33 |
| | 0.01% | 70 | -46 |
| | 0.001% | 43 | -40 |
| *Bifidus* | 10% | 107 | 546 |
| *Lactobacillus* | 5% | 200 | 245 |
| Dhatelo oil | 0.1% | 63 | 83 |

*percentages shown as a negative number indicate an increase in Inflammatory Metabolites or Inflammatory Metabolite Markers

SEQUENCE LISTING

<160> NUMBER OF SEQ ID NOS: 7

<210> SEQ ID NO 1
<211> LENGTH: 13

```
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
<222> LOCATION: (1)..(4)
<223> OTHER INFORMATION: Xaa can be any naturally occurring amino acid
      or no amino acid
<220> FEATURE:
<221> NAME/KEY: misc_feature
<222> LOCATION: (5)
<223> OTHER INFORMATION: Xaa can be threonine or serine or no amino acid
<220> FEATURE:
<221> NAME/KEY: misc_feature
<222> LOCATION: (9)
<223> OTHER INFORMATION: Xaa can be isoleucine, leucine, proline,
      valine, alanine, glycine or no amino acid
<220> FEATURE:
<221> NAME/KEY: misc_feature
<222> LOCATION: (10)..(13)
<223> OTHER INFORMATION: Xaa can be any naturally occurring amino acid
      or no amino acid

<400> SEQUENCE: 1

Xaa Xaa Xaa Xaa Xaa Ser Thr Pro Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CLOCK and/or PER1 gene activator

<400> SEQUENCE: 2

Tyr Val Ser Thr Pro Tyr Asn
1               5

<210> SEQ ID NO 3
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 3

Val Ser Thr Pro Glu
1               5

<210> SEQ ID NO 4
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 4

Leu His Ser Thr Pro Pro
1               5

<210> SEQ ID NO 5
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 5

Arg His Ser Thr Pro Glu
```

```
<210> SEQ ID NO 6
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 6

His Ser Thr Pro Glu
1               5

<210> SEQ ID NO 7
<211> LENGTH: 4
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
<222> LOCATION: (4)
<223> OTHER INFORMATION: The C-terminus carboxyl group of Gln is
      replaced with NH2

<400> SEQUENCE: 7

Ser Pro Leu Gln
1
```

METHODS AND COMPOSITIONS FOR TREATING SKIN TO RESOLVE INFLAMMATION AND SCREENING FOR ACTIVES THAT STIMULATE PRO-RESOLUTION PATHWAYS

TECHNICAL FIELD

The invention is in the field of methods, compositions, screening processes for treating keratin surfaces to stimulate inherent cellular pro-resolution pathways so that inflammatory skin conditions can be normalized.

BACKGROUND OF THE INVENTION

Skin is the largest and one of the most complex body organs. It comprises from about 15 to 20% of the entire body weight and serves as a protective barrier to environmental toxins and assaults. Skin that is in good health is referred to as normalized. The skin's immune response to environmental conditions such as excessive sun exposure, cold weather, wind, or cigarette smoke can cause skin to become irritated or inflamed—in other words the skin is no longer normalized. For years cosmetics manufacturers have sold products for normalizing skin that included ingredients believed to have anti-inflammatory or anti-irritant properties. However, since there are a myriad of biological reactive pathways that contribute to skin inflammation and these products often contained ingredients that did not have any impact on any of these reactive pathways, they were not often as effective as they could have been. In other words, to effectively treat irritated or inflamed skin it is important to understand the biological pathways that contribute to the situation to begin with. Then active ingredients that exert a positive effect on blocking inflammatory pathways or stimulating pathways that promote resolution of the inflammatory state can be formulated into topical products.

Inflammation is a defense mechanism in organisms. There are 3 distinct phases of inflammation: the initiation phase, the amplification phase, and a resolution phase. The inflammatory process generates oxidized polyunsaturated fatty acids (PUFA) which have a role in stimulating the release of lipid mediators that assist in resolution of the inflammation, also referred to as pro-resolution lipid mediators. Examples of such pro-resolution lipid mediators include Resolvins, Maresins, Lipoxins, and Protectins.

In order to assess the efficacy of an active ingredient in resolving inflammation, accurate measurement of the various lipid mediators that are markers for the inflammatory state is necessary. To create products that contain active ingredients that exert a positive effect on the pro-resolution pathways to reduce the incidence and duration of inflammation is a very desirable commercial goal. However, one challenge is that measuring the effectiveness of an active ingredient on human test subjects challenged with inflammatory stimuli and observed for response is not always scientifically accurate since each individual differs in terms of sensitivity and immune response to challenge. It has been found that measuring certain PUFA markers will indicate the presence and concentration of various lipid mediators known to be involved in resolution of inflammation. It is one way to screen and identify actives that, when applied to skin, are capable of stimulating the release of skin's natural pro-resolution lipid mediators such as Resolvins, Maresins, Protectins, or Lipoxins, to reduce the incidence, duration, and severity of the inflammatory response.

It is an object of the invention to identify active ingredients that are effective in treating individuals with inflamed skin in need of normalization by stimulating the skin's natural pro-resolution lipid pathway.

It is a further object of the invention to provide a method and compositions for normalizing inflamed skin in an individual by topically applying actives that stimulate the skin's pro-resolution pathways and cause the skin to secrete pro-resolution lipid mediators in an amount sufficient to improve the condition of the skin.

SUMMARY OF THE INVENTION

The invention is directed to a composition comprising at least one Pro-Resolution Pathway Stimulator selected from an Inflammatory Metabolite Inhibitor, a Pro-Resolving Activator, or combinations thereof.

The invention is also directed to a method for treating an individual having inflamed skin in need of normalization by topically applying a composition containing at least one Pro-Resolution Pathway Stimulator in an amount sufficient to cause the inflamed skin of the treated individual to show:
(a) a decrease in cellular concentration of Inflammatory Metabolites or (b) an increase cellular secretion of Pro-Resolving Lipid Mediators, or both (a) and (b), in an amount effective to normalize the skin The invention is also directed to a method for formulating a topical skin care composition containing one or more Pro-Resolution Pathway Stimulators by:
  (a) selecting an active ingredient;
  (b) quantifying the inhibition in release of one or more Inflammatory Metabolites or Inflammatory Metabolite Markers from cells to which the active is exposed,
  (c) quantifying the increase in release of one or more Pro-Resolving Lipid Mediators or Pro-Resolving Lipid Mediator Markers in cells exposed to the active,
  (d) selecting the active that shows:
    (i) a decrease in release of Inflammatory Metabolites or Inflammatory Metabolite Markers individually or in combination; or
    (ii) an increase in release of Pro-Resolving Lipid Mediators or Pro-Resolving Lipid Mediator Markers individually or in combination
  (e) formulating the active selected in (d) into topical cosmetic products.

The invention is also directed to a method for formulating a topical skin care composition containing one or more Pro-Resolving Activators by:
  (a) selecting an active ingredient;
  (b) quantifying the increase in release of one or more Pro-Resolving Lipid Mediators or Pro-Resolving Lipid Mediator Markers in cells exposed to the active,
  (d) selecting the active that shows:
    (i) a net positive increase in release of Pro-Resolving Lipid Mediators or Pro-Resolving Lipid Mediator Markers individually or in combination
  (e) formulating the active selected in (d) into topical cosmetic products.

DESCRIPTION OF THE DRAWINGS

FIGS. 1A, B, C, and D: illustrate the results of testing concentrations of actives to determine the most suitable active test concentrations.

FIG. 2: Shows the results of testing various actives with respect ability to inhibit Inflammatory Metabolites or for Pro-Resolving Activator activity.

FIG. 3: shows the aggregate of measurements for Inflammatory Metabolites and Inflammatory Metabolite Markers and Pro-Resolving Lipid Mediator Markers indicative of actives that are Inflammatory Metabolite Inhibitors and/or Pro-Resolving Activators. The shaded cells indicate active and concentrations that are acceptable Inflammatory Metabolite Inhibitors and Pro-Resolving Activators.

DETAILED DESCRIPTION

A. Definitions

All documents referred to herein are incorporated by reference in their entirety.

With all terms, the singular includes the plural and vice versa.

All percentages mentioned herein are percentages by weight unless otherwise indicated.

The term "cells" means cells found in mammalian skin or body including but not limited to keratinocytes, fibroblasts, neutrophils, macrophages, basophils, eosinophils, lymphocytes, muscle cells, neural cells, etc.

The term "14-HDOHE" means 14-hydroxydocosahexaenoic acid.

The term "17-HDOHE" means 17-hydroxydocohexaenoic acid.

The term "18-HEPE" means 18-hydroxyeicosapentaenoic acid.

The term "5-HETE" means 5-hydroxyeicosatetraeonic acid.

The term "12-HETE" means 12-hydroxyeicosatetraeonic acid.

The term "15-HETE" means 15-hydroxyeicosatetraeonic acid.

The term "H-HPETE" means (5-hydroxyperoxyeicosatetraenoic acid)

The term "inflamed" means, with respect to skin, that it exhibits one or more of the indicators of inflammation, which are redness, pain, or heat.

The term "inflammation precipitating condition" means a condition that precipitates inflammation in cells such as skin cells, and that manifests in skin by showing redness, pain, or heat. Examples of such conditions include but are not limited to wind, cold, allergens, dust, smog, pollution, chemicals, heat, abrasions, sun, insect bites and the like Inflammation precipitating conditions may also be induced by exposing cells to agents that are known to precipitate inflammation, such as 5-(methylamino)-2-({(2R,3R,6S,8S,9R,11R)-3,9,11-trimethyl-8-[(1S)-1-methyl-2-oxo-2-(1H-pyrrol-2-yl)ethyl]-1,7-dioxaspiro[5.5]undec-2-yl}methyl)-1,3-benzoxazole-4-carboxylic acid or PMA (phorbol myristate acetate) or both.

The term "Inflammatory Metabolite" means a metabolite secreted by the cell in response to an inflammation precipitating condition and that promotes inflammation. Examples of Inflammatory Metabolites include cyclic endoperoxides derived from arachidonic acid or prostaglandins such as PGI2 (Prostacyclin 12), PGE2 (Prostaglandin E2), PGF2 alpha Prostaglandin F2 alpha), PGA2 (Prostaglandin A2), PGD2 (Prostaglandin D2), or leukotrienes such as LTA4 (Leukotriene A4), LTB4 (Leukotriene B4), LTC4 (Leukotriene C4), LTD4 (Leukotriene D4), or Platelet Activating Factor (PAF). Other Inflammatory Metabolites include peptides in the form of cytokines and chemokines such as IL-1 alpha (Interleukin-1 alpha), IL-1 beta (Interleukin-1 beta), IL-6 (Interleukin-6), IL-8 (Interleukin-8), TNF alpha (tumor necrosis factor), and MCP-1 (monocyte chemotactic protein-1).

The term "Inflammatory Metabolite Inhibitor" means an active ingredient that, when applied to skin cells, causes the cells to inhibit secretion of Inflammatory Metabolites.

The term "Inflammatory Metabolite Marker" means a metabolite, generally precursors or intermediates in the reaction scheme that ultimately yields Inflammatory Metabolites. This reaction scheme commences upon exposure of cells to an inflammation precipitating condition, and serves as a marker for the presence of the Inflammatory Metabolite. An example of an Inflammatory Metabolite Marker includes 5-HETE, H-HPETE, and other hydroperoxides such as LTA4, LTC4, LTD, LTE4. Also suitable as Inflammatory Metabolite Inhibitors are PGG2, PGH2, endoperoxide precursors of PGE2 and other derivatives of PGH2 such as PGD2, PGD2, PGI2, PGF2 alpha and 6-keto PGF1 alpha.

The term "Lipoxins" means "lipoxygenase interaction products" which are Pro-Resolving Lipid Mediators derived from arachidonic acid, and is an eicosanoid, a class of signaling molecules derived from oxidation of omega-3 or omega-6 fatty acids. Generally the appearance of Lipoxin in the inflammation cascade indicates that the inflammatory condition has been resolved. One example of a Lipoxin has the following structure:

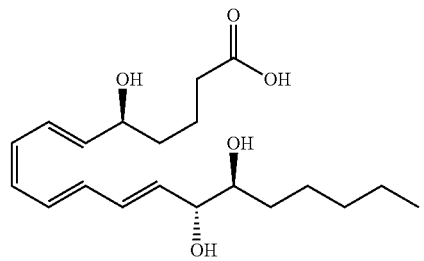 [SMILES: CCCCC[C@H](O)[C@H](O)/C=C/C=C/C=C\C=C\[C@@H](O)CCCC(=O)O]

The term "LT" means leukotriene, with the designation after "LT" referring to the type. For example, LTA4 means Leukotriene A4, LTB4 means Leukotriene B4, LTD means Leukotriene D, and so on.

The term "Maresin" means "macrophage mediator in resolving inflammation" which is made by the body from the essential fatty acid docosahexaenoic acid. Maresins have very potent anti-inflammatory and pro-resolving activity, similar to Resolvins. Maresins are Pro-Resolving Lipid Mediators. One example of a Maresin is 7-S Maresin having the formula:

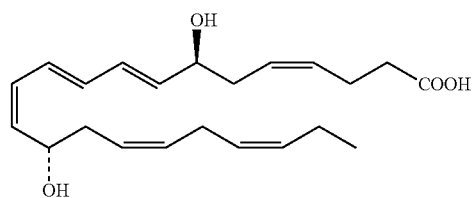 [SMILES: CC/C=C\C/C=C\C[C@H](O)\C=C/C=C/C=C/[C@@H](O)C/C=C\CCC(=O)O]

The term "normalization" or "normalized" means, with respect to skin, that the skin exhibits a normal healthy state not having the indicators associated with inflamed skin.

The term "PG" means "Prostaglandin" with the designation (usually alpha numeric) after PG referring to the type.

For example, PGE2 means Prostaglandin E2, PGG2 means Prostaglandin G2, and PGI2 means Prostaglandin 12 and so on.

The term "Pro-Resolving Activator" means an active ingredient that stimulates the release of Pro-Resolving Lipid Mediators (such as Resolvins, Protectins, Lipoxins, and Maresins) from cells that may or may not have been exposed to inflammation precipitating conditions.

The term "Pro-Resolving Lipid Mediator" means a metabolite secreted from skin cells has that has pro-resolving activity, that is, activity that promotes resolution of the inflammatory state. Generally, an increase in cellular Pro-Resolving Lipid Mediator concentration positively correlates with resolution of the inflammatory state. Examples of Pro-Resolving Lipid Mediators include Resolvins, Protectins, Lipoxins, and Maresins.

The term "Pro-Resolving Lipid Mediator Marker" means a metabolites, generally precursors or intermediates in the reaction scheme that yields Pro-Resolving Lipid Mediators. Upon exposure to events that precipitate inflammation, enzymes such as cyclooxygenase (COX), Lipoxygenase (LOX), Cytochrome Epoxygenase (CYPe) and Cytochrome Hydrolase (CYP) metabolize fatty acids found at the site (such as arachidonic acid ("AA") or eicosapentaenoic acid ("EPA")) in a reaction scheme that ultimately generates Pro-Resolving Lipid Mediators through various precursors in the reaction scheme. Examples of Pro-Resolving Lipid Mediator Markers and precursors in the reaction scheme that yields Pro-Resolving Lipid Mediators include 15-HETE, 12-HETE, 14-HDOHE, 18-HEPE, or 17-HDOHE. Measuring Pro-Resolving Lipid Mediator Markers is indicative of, and quantitative for, the concentration of Pro-Resolving Lipid Mediators released by cells.

The term "Pro-Resolution Pathway Stimulator" means an active ingredient that is: (a) an Inflammatory Metabolite Inhibitor or (b) a Pro-Resolving Activator, or both.

The term "Protectins" means, in particular, protectin D1 or neuroprotectin D1, which are autocoids. Protectins have very strong anti-inflammatory activity and are produced in the body by oxidation of Omega-3 fatty acids. Autacoids are short duration biological actives that act near their site of synthesis. Protectins are Pro-Resolving Lipid Mediators. One example of a Protectin has the following formula:

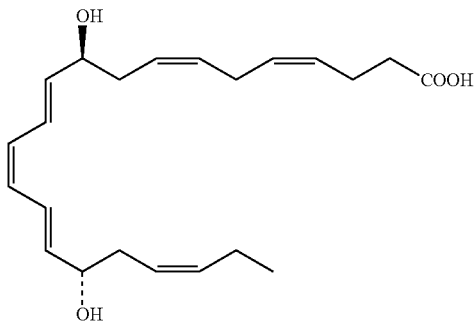 [SMILES: CC/C=C\C[C@H](O)/C=C/C=C\C=C\[C@@H](O)C/C=C\C/C=C\CCC(=O)O]

The term "Resolvin" means "resolution phase interactive products" which are made by the body from the Omega-3 fatty acids, eicosapentaenoic acid and docosahexaenoic acid. They are produced by the COX-2 (cyclooxygenase-2) or other enzymatic pathways. Resolvins are Pro-Resolving Lipid Mediators. An example of a Resolvin includes one having the following formula:

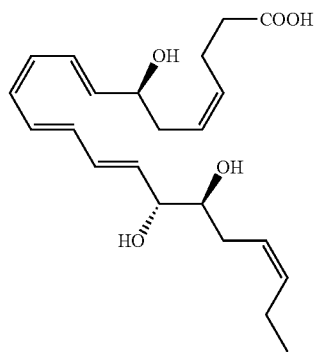 [SMILES: CC/C=C\C[C@H](O)[C@H](O)/C=C/C=C/C=C\C=C\[C@@H](O)C/C=C\CCC(=O)O]

B. A Method for Treating Skin

The invention is directed to a method for treating an individual having inflamed skin in need of normalization by topically applying a composition containing at least one Pro-Resolution Pathway Stimulator in an amount sufficient to cause the inflamed skin of the treated individual to show: (a) a decrease in cellular concentration of Inflammatory Metabolites, or (b) an increase cellular secretion of Pro-Resolving Lipid Mediators, or both, in an amount effective to normalize the skin.

The Pro-Resolution Pathway Stimulator may be Inflammatory Metabolite Inhibitor and/or a Pro-Resolving Activator. Preferred is where the active ingredient is both an Inflammatory Metabolite Inhibitor and a Pro-Resolving Activator. Also preferred is where the composition contains two different actives, one that is an Inflammatory Metabolite Inhibitor and the other a Pro-Resolving Activator.

In one embodiment of the invention the Pro-Resolving Activator is not a Pro-Resolution Lipid Mediator or a Pro-Resolution Lipid Mediator Marker. In other words, the Pro-Resolving Activator demonstrates the desired activity by promoting the treated skin cells to secrete Pro-Resolution Lipid Mediators rather promoting the inflammation resolution state by applying Pro-Resolution Lipid Mediators or Pro-Resolution Lipid Mediator Markers directly to the skin to supplement the Pro-Resolution Lipid Mediators or Pro-Resolution Lipid Mediator Markers that are already secreted by skin.

Inflammatory Metabolite Inhibitors can be identified by screening actives for their ability to inhibit release of Inflammatory Metabolites from cells that are exposed to inflammation precipitating events. The ability to inhibit release of Inflammatory Metabolites may be assessed by measuring the cellular concentration of the Inflammatory Metabolites themselves or measuring Inflammatory Metabolite Markers which are markers for the presence of Inflammatory Metabolites. The measurement of the Inflammatory Metabolites or Inflammatory Metabolite Markers may be performed on untreated cells to obtain a baseline reading. The cells may be exposed to an inflammation precipitating condition either before or after exposure to the active ingredient. In one embodiment the cells are exposed to the inflammation precipitating condition and the cellular concentration of Inflammatory Metabolites and/or Inflammatory Metabolite Markers is measured. Preferred is where the Inflammatory Metabolites that are measured include Prostaglandins, Leukotrienes, or both, in particular PGE2 or LBT4, or the Inflammatory Metabolite Marker measured is 5-HETE. The cellular concentration of Prostaglandins, Leukotrienes, or PGE2, LBT4 or 5-HETE is measured in untreated cells, cells that have been exposed to an inflammation precipitating condition, and cells treated with the active either before or after exposure to the inflammation precipitating condition. The cellular concentration of PGE2, LBT4 or 5-HETE is measured. Active ingredients that cause a net decrease in cellular concentration of PGE2, LBT4, or 5-HETE either individually or in combination when exposed to the active are suitable Inflammatory Metabolite Inhibitors.

More specifically, suitable Inflammatory Metabolite Inhibitors can be identified by screening active ingredients as follows:
(a) selecting cells to be tested
(b) subjecting the cells in (a) to an inflammation precipitating condition,
(c) measuring the cellular concentration of Inflammatory Metabolites (by measuring the Inflammatory Metabolite concentration by itself) or measuring Inflammatory Metabolite Markers (which are indicative of the presence of Inflammatory Metabolites),
(d) exposing the cells to an active,
(e) measuring the cellular concentration of Inflammatory Metabolites or Inflammatory Metabolite Markers,
(f) selecting the active as an Inflammatory Metabolite Inhibitor if it shows a net decrease in cellular concentration of Inflammatory Metabolites or Inflammatory Metabolite Markers after exposure to the active.

Alternatively, the cells can be pre-treated with active ingredient and the cellular concentration of Inflammatory Metabolites or Inflammatory Metabolites Markers measured. Control cells and active-treated cells are then exposed to an inflammation precipitating condition and the concentration of Inflammatory Metabolites and/or Inflammatory Metabolite Markers is measured again. An active that is a suitable Inflammatory Metabolite Inhibitor is one where there is a net decrease in cellular concentration of Inflammatory Metabolites or Inflammatory Metabolite Markers in response to exposure of the cells to the active when compared to the untreated control cells that are subjected only to the inflammation precipitating condition.

More preferred is when the decrease in cellular concentration of Inflammatory Metabolites and/or Inflammatory Metabolite Makers when expressed as a percentage in comparison to cellular concentrations for the same cells exposed only to the inflammation precipitating condition ranges from 1 to 1000% more preferably 10 to 600% more preferably 20 to 300%, or 25 to 250% or even 50 to 200% with all such ranges including all whole integers in between.

Pro-Resolving Activators can be identified by screening actives for their ability to increase cellular concentration or secretion of Pro-Resolving Lipid Mediators. The presence of Pro-Resolving Lipid Mediators can be assessed by measuring cellular concentration of Pro-Resolving Lipid Mediators themselves or Pro-Resolving Lipid Mediator Markers.

Suitable Pro-Resolving Activators can be identified by screening active ingredients as follows:
(a) selecting cells to be tested
(b) subjecting the cells in (a) to an inflammation precipitating condition,
(c) measuring the cellular concentration of Pro-Resolving Lipid Mediators or Pro-Resolving Lipid Mediator Markers,
(d) selecting an active as a Pro-Resolving Activator if it shows a net increase in cellular concentration of Pro-Resolving Lipid Mediators or Pro-Resolving Lipid Mediator Markers of after exposure to the active.

Alternatively, the cells can be pre-treated with active ingredient and the cellular concentration of Pro-Resolving Lipid Mediators or Pro-Resolving Lipid Mediator Markers measured. Control cells and active-treated cells are then exposed to an inflammation precipitating condition and the concentration of Pro-Resolving Lipid Mediators or Pro-Resolving Lipid Mediator Markers is measured again. An active is a suitable Pro-Resolving Activator if it shows a net increase in cellular concentration of Pro-Resolving Lipid Mediators or Pro-Resolving Lipid Mediator Markers in response to exposure of the cells to the active and when compared to the untreated control cells that are subjected only to the inflammation precipitating condition.

Examples of Pro-Resolving Lipid Mediator Markers include one or more of 15-HETE, 12-HETE, 14-HDOHE, 18-HEPE, or 17-HDOHE. More preferred is where the increase in cellular concentration of Pro-Resolving Lipid Mediators or Pro-Resolving Lipid Mediator Markers when measured alone or in the aggregate show an increase ranging from 1 to 1000%, preferably 5-600%, more preferably 10 to 550%, or even 5 to 550% when expressed as a percentage increase in cellular concentration when compared to cells treated only to the inflammation precipitating condition. This range includes all whole integers in the range.

Examples of Pro-Resolution Pathway Stimulators

Active ingredients may include chemical compounds, compositions, botanical extracts, or any ingredient or ingredient combination desired. The Pro-Resolution Pathway Stimulators may be Inflammatory Metabolite Inhibitors, Pro-Resolving Activators, or both. In some cases the active may be only an Inflammatory Metabolite Inhibitor or a Pro-Resolving Activator but not both. Most preferred is where the active is both an Inflammatory Metabolite Inhibitor and a Pro-Resolving Activator, and where the Inflammatory Metabolite Inhibitor when exposed to cells subjected to an inflammation precipitating condition, shows a decrease in the release of Inflammatory Metabolites or Markers that is greater than 1% all the way up to 1000% with this range including all sub ranges and whole integers in between. More specifically the percentage decrease may range from 1 to 600%, preferably from 10 to 500%, more preferably from 20 to 300%, even 50 to 250% when compared to measurement of control cells exposed only to the inflammation precipitating condition.

Suitable Pro-Resolving Activators are those that show an increase in cellular concentration of Pro-Resolving Lipid Mediators or Markers therefore that is greater than 1% all the way up to 1000% when compared to cells treated only with the inflammation precipitating condition. More specifically, the percentage increase in cellular concentration of Pro-Resolving Lipid Mediators or Pro-Resolving Lipid Mediator Markers may range from 1 to 600%, preferably from about 5 to 550%, more preferably from 10 to 550%, more preferably from 20 to 550%, or even from 100 to 550%.

Further specific examples of Inflammatory Metabolite Inhibitors and/or Pro-Resolving Activators include, but are not limited to:

Inactivated Cultures of *Bifidobacterium*

Inactivated cultures of *Bifidobacterium* may be made according to the process set forth in U.S. Pat. No. 4,464,362. The *Bifidobacterium* may originate from a variety of species. Preferably the species are those that confer the "probiotic" designation. Most preferred is where the species is *Bifidobacterium longum*. More specific examples of *Bifido-*

*bacterium* are referred to by their INCI names, e.g. Bifida lysate, Bifida ferment lysate, Bifida filtrate, and so on. Also suitable are Bifida extract, which is an extract obtained from the fermentation of *Bifidobacterium longum*, and Bifida ferment filtrate which is a filtrate of the product obtained by fermentation of Bifida. Most preferred is Bifida ferment lysate, which is a product obtained by the fermentation of Bifida. Also suitable are mixtures containing inactivated cultures of *Bifidobacterium* or ferments thereof.

*Lactobacillus*

Also suitable are various active or inactivated cultures from various species of *Lactobacillus*, another organism that is often referred to as "probiotic". The *Lactobacillus* may be in the form of ferments, lysates, or filtrates either alone or in combination with other ingredients. Preferred is a fermentation product of *Lactobacillus*. The *Lactobacillus* may also be part of a mixture with other probiotic ingredients, ferments, filtrates, and the like.

Alpha or Beta Hydroxy Acids or Esters

Alpha or beta hydroxy acids or esters thereof are examples of suitable Inflammatory Metabolite Inhibitors and/or Pro-Resolving Activators. Suitable alpha or beta hydroxy acids include those disclosed in U.S. Pat. No. 5,422,370 that may include glycolic, lactic, salicylic, mandelic, tartaric, acids or C1-30, preferably C6-22, more preferably C16-20 straight or branched chain aliphatic or aromatic esters thereof such as octyl salicylate, palmitoyl lactate, steary lactate, and so on. Also suitable are derivatives of alpha or beta hydroxyl acids such as amides, amines, and so on. Particularly preferred is salicylic acid.

Resveratrol Esters

Also suitable are resveratrol esters including those disclosed in U.S. Pat. No. 8,084,496 and U.S. Patent Application No. 2010/0215755. More specifically these resveratrol esters have the general formula:

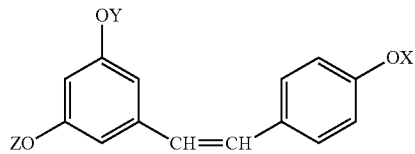

Where X, Y, and Z are each independently wherein X, Y, and Z are either hydrogen or a protective group, provided that at least one of X, Y, and Z is the protective group. More preferred is where one or more of X, Y, and Z are carboxylic acid esters, preferably carboxylic fatty acid esters such as those having from 6 to 30, preferably 12 to 22 carbon atoms, and where the carboxylic fatty acid esters may be saturated or unsaturated.

Particularly preferred resveratrol esters are resveratrol ferulate, resveratrol ascorbate, and resveratrol salicylate. Resveratrol ferulate, resveratrol ascorbate and resveratrol salicylate may be manufactured by the methods set forth in above patents or patent applications.

Botanical Extracts and Oils

Further examples of actives are botanical extracts and oils from genuses such as *Poria, Dongbaek, Camellina, Aleurites, Perilla, Dhatelo* and the like. More specifically botanical extracts and oils may be selected from *Poria cocos* oil and extract, *Dongbaek* (Tsubaki) oil, *Camellina sativa, Aleurites Moluccana* (Kukui) seed oil, *Perilla ocyimoides* extract, *Dhatelo* oil, algae extract, *Laminaria digitata*, and so on. Also, any botanical ingredient extract that contains Omega-3 fatty acids or Omega-6 fatty acids would also be suitable. Such botanical extracts may be obtained by extraction with water, short chains alcohols such as methanol or ethanol, or by mixtures of water and alcohols.

In one embodiment of the invention the Pro-Resolution Pathway Stimulator may be an Omega-3 or Omega-6 fatty acid or derivative thereof. Omega-3 fatty acids include Hexadecatrienoic acid, α-Linolenic acid, Stearidonic acid, Eicosatrienoic acid, Eicosatetraeonic acid, Eicosapentaenoic acid, Heneicosapentaenoic acid, Docosapentaenoic acid, Docosahexaenoic acid, Tetracosapentaenoic acid, or Tetracosahexaenoic acid. Omega-6 fatty acids include Linoleic acid, Gamma-linoleic acid, Calendic acid, Eicosadienoic acid, Dihomo-gamma-gamma-linolenic acid, Arachidonic acid, Docosadienoic acid, Adrenic acid, Docosapentaenoic acid, Tetracosatetraenoic acid, Tetracosapentaenoic acid.

B. A Method for Formulating a Topical Product

The invention comprises a method for formulating a topical product for treating inflamed skin by identifying one or more Pro-Resolution Pathway Stimulators and formulating them into a topical product.

More specifically, the invention is directed to a method for formulating a topical composition containing one or more Pro-Resolution Pathway Stimulators by (a) selecting an active ingredient; (b) quantifying the inhibition in cellular concentration of one or more Inflammatory Metabolites or Inflammatory Metabolite Markers from cells to which the active is exposed, (c) quantifying the increase in cellular concentration of one or more Pro-Resolving Lipid Mediators or Pro-Resolving Lipid Mediator Markers in cells exposed to the active, (d) selecting the active that shows: (i) a net decrease in cellular concentration of Inflammatory Metabolites or Inflammatory Metabolite Markers individually or in combination; or (ii) a net increase in release of Pro-Resolving Lipid Mediators or Pro-Resolving Lipid Mediator Markers individually or in combination; and (e) formulating the active selected in (d) into topical cosmetic products.

The amount of active ingredient to be tested is determined by running cellular toxicity tests using the cell selected for the testing. Such cellular toxicity testing involves exposing the cells in diluents such as culture media, DMSO, or an inert solvent, to serial dilutions of the active which may also be diluted in the appropriate inert solvent. The active concentrations prior to the concentration where cellular toxicity is beginning to evidence are most optimal for testing.

Inflammatory Metabolites from Prostaglandin or Leukotriene family (e.g. PGE2 and LTB4) positively correlate with inflammation, as does Inflammatory Metabolite Marker 5-HETE. Accordingly increasing cellular concentrations of PGE2, LTB4, or 5-HETE correlate with increasing inflammation. Actives that are Inflammatory Metabolite Inhibitors of PGE2, LTB4, will cause cellular concentration of Inflammatory Metabolites or their Markers to decrease when contact with cells that have been exposed to an inflammation precipitating condition. On the other hand, Pro-Resolving Lipid Mediators and Pro-Resolving Lipid Mediator Markers are associated with resolution of inflammation. Thus, increasing levels of Pro-Resolving Lipid Mediators or their Markers correlate with a reduction in cellular inflammation and an increase in resolution of inflammation by increasing secretion of the Pro-Resolution Lipid Mediators such as Maresin, Lipoxin, Resolvin, or Protectin.

The invention is also directed to method for identifying Inflammatory Metabolite Inhibitors, and Pro-Resolving Activators by screening actives for each parameter separately.

For example, in one embodiment the invention is the invention is directed to a method for formulating a topical skin care composition containing one or more Pro-Resolving Lipid Mediators by:

(a) selecting an active ingredient;
(b) quantifying the increase in release of one or more Pro-Resolving Lipid Mediators or Pro-Resolving Lipid Mediator Markers in cells exposed to the active,
(d) selecting the active that shows:
(i) a net positive increase in release of Pro-Resolving Lipid Mediators or Pro-Resolving Lipid Mediator Markers individually or in combination
(c) formulating the active selected in (d) into topical cosmetic products.

The percentage increases in cellular concentration of actives, and examples of actives that may be suitable Pro-Resolving Activators are as set forth above.

The invention is also directed to a method for screening for Inflammatory Metabolite Inhibitors by:
(a) selecting cells to be tested
(b) subjecting the cells in (a) to an inflammation precipitating condition,
(c) measuring the cellular concentration of Inflammatory Metabolites or Inflammatory Metabolite Markers,
(d) exposing the cells to an active,
(e) measuring the cellular concentration of Inflammatory Metabolites or Inflammatory Metabolite Markers,
(f) selecting the active as an Inflammatory Metabolite Inhibitor if it shows a net decrease in cellular concentration of Inflammatory Metabolites or Inflammatory Metabolite Markers after exposure to the active.

The percentage decrease in cellular concentration of Inflammatory Metabolites or Markers in cells treated with active, and suitable actives, as set forth above.

The method of the invention is suitable for screening large numbers of active ingredients and identifying their efficacy as either Pro-Resolving Activators or Inflammatory Metabolite Inhibitors, and formulating them into products for the treatment of keratin surfaces such as skin, hair, or nail, but preferably skin.

C. The Composition

The invention is directed to a composition comprising at least one Pro-Resolution Pathway Stimulator selected from an Inflammatory Metabolite Inhibitor, a Pro-Resolving Activator, or combinations thereof.

Examples of Pro-Resolution Pathway Stimulators include those set forth above. Recommended concentrations of Pro-Resolution Pathway Stimulators range from 0.0001 to 15%, preferably from 0.005 to 10%, more preferably from 0.01 to 5%, or 0.1 to 2% by weight of the total composition. Alternatively concentration in the topical composition may be expressed as µg/ml with suitable concentrations of active ranging from 0.1 to 250 µg/ml, preferably from 0.5 to 200 µg/ml, more preferably from 1 to 150 µg/ml.

Examples of Inflammatory Metabolite Inhibitors include those set forth above. Recommended concentration ranges of Inflammatory Metabolite Inhibitors may range from 0.00001 to 10%, more preferably from 0.0005 to 8%, more preferably from 0.0001 to 5%.

The composition may be in the form of a product for application to skin, hair, or nails and may be in the anhydrous, emulsion or aqueous solution or suspension form. The composition may be a liquid, solid, or semi-solid with such consistencies referred to for room temperature (25° C.).

The composition of the invention may be in the form of an emulsion, aqueous solution or dispersion, gel, or anhydrous composition. If in the form of an emulsion, it may be a water in oil or oil in water emulsion. If in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

The composition may optionally contain the following ingredients:

Autophagy Activators

The composition of the invention may contain at least one ingredient that is operable to activate normal cellular autophagic processes. If present the autophagy activator may range from about 0.00001 to 20%, preferably 0.0001-5%, more preferably from about 0.001 to 1%. In general, the cellular autophagy process comprises four general steps. Step 1 is the initiation of vacuole formation; Step 2 the formation of the initial vacuole or autophagosome which sequesters the cytoplasmic material to be degraded. Step 3 is the maturation of the autophagosome into a degradative vacuole. Step 4 is the actual degradation of the sequestered material.

Ingredients with autophagy activation activity can be identified by their ability to either stimulate or inhibit various cellular metabolic pathways. For example, ingredients that stimulate the expression of MAP-LC3, ATG5-12, protein p53, AMPK, or DRAM are suitable autophagy activators. Ingredients that inhibit the expression of mTOR are also suitable autophagy activators.

The gene MAP-LC3 codes for microtubule-associated protein 1 light chain 3, a protein that initiates formation of autophagosomes. ATG5-12 also stimulates formation of autophagosomes. mTOR, also known as mammalian target of rapamycin, is also known as the mechanistic target of rapamycin or FK506 binding protein 12-rapamycin associated protein 1 (FRAP1). FRAP1 is encoded by the FRAP gene. Any ingredient that inhibits the expression of mTOR, involved in autophagosome creation, will have autophagy activating properties. Also suitable as autophagy activators are ingredients that stimulate expression of protein p53, AMPK, and/or DRAM (damage remedy autophagy modulator protein) in keratinocytes. Protein p53, also known as a tumor suppressor protein, is encoded by the p53 gene. AMPK means AMP activated protein kinase and DRAM, damage related autophagy modulator. Both are known to stimulate autophagy activation in keratinocytes.

Thus any ingredient that has the above mentioned effects on the genes may be suitable autophagy activators. During the autophagocytic process cellular debris such as oxidized proteins and peroxidized lipids are degraded. Such cellular debris often affects normal metabolic function. Screening of ingredients to determine efficacy by ability to stimulate or inhibit cellular, preferably keratinocyte, genes and/or proteins mentioned above may be done according to methods as set forth in US Patent Publication No. 2011/0243983 or other methods known in the art.

For example, one general process for identifying ingredients that may be autophagy activators is by first inducing nutritive stress in cultured cells such as keratinocytes. For example, the cells are first cultured in complete culture medium with growth factors, for about 24 hours. The culture medium is then removed and replaced with a non-nutritive culture medium, for example one that does not contain growth factors. The cells are cultured for about 30 minutes to about 25 hours in a state of nutritive stress. Then, the non-nutritive culture medium is removed and replaced with complete culture medium to promote cellular recovery. Thereafter, the cells are evaluated for autophagocytic activity by measuring the expression of one or more of MAP-LC3; ATGS-12; phosphorylated mTOR; phosphorylated p53; DRAM; or phosphorylated AMPK in those cells. Measurement of such expression can take place by immunofluorescence measurements. In addition, the expression can be ascertained by Western Blot analysis of phosphorylated proteins associated with the expressed genes.

Examples of ingredients that are known to exert either the stimulatory or inhibitory effects on the above mentioned genes which, in turn, stimulate autophagy, are yeast extracts including but not limited to those from the genuses such as *Lithothamnium, Melilot, Citrus, Candida, Lens, Urtica, Carambola, Momordica, Yarrowia, Plumbago*, etc. Further specific examples include *Lithothamniumn calcaneum, Melilotus officinalis, Citrus limonum, Candida saitoana, Lens culinaria, Urtica dioica, Averrhoa carambola, Momordica charantia, Yarrowia lipolytica, Plumbago zeylanica* and so on.

Also suitable are ingredients such as amiodarone hydrochloride, GF 109203X which is also referred to as (3-(N-[Dimethylamino]propyl-3-indolyl)-4-(3-indolyl)maleimide 3-[1-[3-(Dimethylamino)propyl]1H-indol-3-yl]-4-(1Hindol-3-yl)1H-pyrrole-2,5dione Bisindolylmaleimide I; N-Hexanoyl-D-sphingosine; Niclosamide; Rapamycin from *Streptomyces hygroscopicus*; Rottlerin which is also referred to as (1-[6-[(3-Acetyl-2,4,6-trihydroxy-5-methylphenyl) methyl]-5,7-dihydroxy-2,2-dimethyl-2H-1-benzopyran-8-yl]-3-phenyl-2-propen-1-one, Mallotoxin); STF-62247, also known as 5-Pyridin-4-yl-thiazol-2-yl-m-tolyl-amine; Tamoxifen; Temsirolimus which is also known as 42-[3-Hydroxy-2-methylpropanoate, CCI-779, Rapamycin; ATG1 autophagy related 1 homolog; ATG1, Serine/threonine-protein kinase ULK1, UNC-51-like kinase; or Z36 which is also referred to as ((Z)-5-Fluoro-1-(3'-dimethylamino)propyl-3-[(5-methoxyindol-3-ylidene)methyl]-indolin-2-one; or 1-[3-(dimethylamino)propyl]-5-fluoro-1,3-dihydro-3-[(5-methoxy-1H-indol-3-yl)methylene]-2H-Indol-2-one); Bufalin, also referred to as 3β,14-Dihydroxy-5β,20(22)-bufadienolide, 5β,20(22)-Bufadienolide-3β,14-diol. Such ingredients may be purchased from Sigma-Aldrich Chemical Company.

Proteasome Activators

The composition may also contain a proteasome activator in an amount ranging from about 0.0001 to 65%, preferably from about 0.0005 to 50%, more preferably from about 0.001 to 40%.

Suitable proteasome activators are any compounds, molecules, or active ingredients that stimulate proteasome activity in the cells of keratin surfaces.

Examples of suitable proteasome activators include, but are not limited to, algin, alginates, hydrolyzed algin, molasses extract, *Trametes* extracts, including extracts from *Trametes versicolor*, olea hydroxol.

CLOCK, PER1 Gene Activators

The composition of the invention may contain a CLOCK or PER1 cellular gene activator. Suggested ranges are from about 0.000001 to about 40%, preferably from about 0.000005 to 35%, more preferably from about 0.00001 to 25%. Suitable CLOCK or PER1 activators may be present in the form of botanical extracts, polypeptides, peptides, amino acids, and the like.

1. Peptide CLOCK or PER1 Gene Activator

A particularly preferred CLOCK and/or PER1 gene activator comprises a peptide of the formula (I):

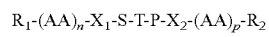

$R_1$-$(AA)_n$-$X_1$-S-T-P-$X_2$-$(AA)_p$-$R_2$ where $(AA)_n$-$X_1$-S-T-P-$X_2$-$(AA)_p$ is (SEQ ID No. 1), and:
  $X_1$ represents a threonine, a serine, or is equal to zero,
  $X_2$ represents an isoleucine, leucine, proline, valine, alanine, glycine, or is equal to zero,
  AA represents any amino acid or derivative thereof, and n and p are whole numbers between 0 and 4,
  $R_1$ represents the primary amine function of the N-terminal amino acid, either free or substituted by a protective grouping that may be chosen from either an acetyl group, a benzoyl group, a tosyl group, or a benzyloxycarbonyl group,
  $R_2$ represents the hydroxyl group of the carboxyl function of the C-terminal amino acid, substituted by a protective grouping that may be chosen from either a C1 to C20 alkyl chain or an NH2, NHY, or NYY group with Y representing a C1 to C4 alkyl chain,
wherein the sequence of general formula (I) comprises from about 3 to 13 amino acid residues, said sequence of general formula (I) possibly containing substitutions of amino acids $X_1$ and $X_2$ with other chemically equivalent amino acids; wherein the amino acids are: Alanine (A), Arginine (R), Asparagine (N), Aspartic Acid (D), Cysteine (C), Glutamic Acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V). More preferred, are peptides of the above formula, as follows:

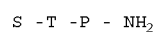

S -T -P - $NH_2$

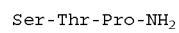

Ser-Thr-Pro-$NH_2$ (SEQ ID No. 2)

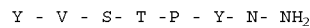

Y - V - S- T -P - Y- N- $NH_2$

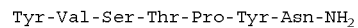

Tyr-Val-Ser-Thr-Pro-Tyr-Asn-$NH_2$ (SEQ ID NO. 3)

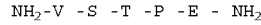

$NH_2$-V -S -T -P -E - $NH_2$

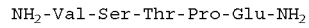

$NH_2$-Val-Ser-Thr-Pro-Glu-$NH_2$ (SEQ ID No. 4)

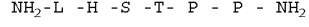

$NH_2$-L -H -S -T- P - P - $NH_2$

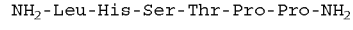

$NH_2$-Leu-His-Ser-Thr-Pro-Pro-$NH_2$

-continued (SEQ ID No. 5)
CH₃NH -R -H -S -T -P -E - NH₂

CH₃-NH-Arg-His-Ser-Thr-Pro-Glu-NH₂

(SEQ ID No. 6)
CH₃NH - H -S -T -P -E - CH₃NH

CH₃-NH-His-Ser-Thr-Pro-Glu-CH₃-NH

More preferred is the S-T-P-NH₂ peptide, SEQ ID No. 4, or mixtures thereof. Most preferred is a peptide manufactured by ISP-Vinscience under the trademark Chronolux® having the INCI name Tripeptide-32 or Chronogen® having the INCI name Tetrapeptide-26, which has an amino acid sequence of Ser-Pro-Leu-Gln-NH₂.

2. Botanical Extracts

Also suitable as the CLOCK or PER1 gene activator is cichoric acid or isomers or derivatives thereof. Cichoric acid may be synthetic or naturally derived. Synthetic cichoric acid may be purchased from a number of commercial manufacturers including Sigma Aldrich. Cichoric acid may also be extracted from botanical sources that are known to contain cichoric acid such as *Echinacea, Cichorium, Taraxacum, Ocimum, Melissa*, or from algae or sea grasses. More specifically, botanical extracts such as *Echinacea purpurea, Cichorium intybus, Taraxacum officinale, Ocimum basilicum*, or *Melissa officinalis*. The term "cichoric acid" when used herein also includes any isomers thereof that are operable to increase PER1 gene expression in skin cells.

One example of a botanical extract is *Echinacea purpurea* sold by Symrise under the brand name Symfinity™ 1298 which is an extract of *Echinacea purpurea* which is standardized during the extraction process to contain about 3% by weight of the total extract composition of cichoric acid. *Echinacea* extracts from different sources will vary in cichoric acid content, and as such will yield variable results in induction of PER1 gene expression. For example, it is known that another component commonly found in extracts of *Echinacea*, specifically caftaric acid, does not increase PER1 gene expression in skin cells. Moreover, each species of *Echinacea* will differ in content of phenolic and cichoric acids. Ethanolic extract of the roots of *Echinacea purpura* will provide more cichoric acid than ethanolic extracts of *Echineacea angustifolia* or *Echinacea pallida*. The content of active ingredients in any extract is also very dependent on the method of extraction. For example, it is known that in many cases enzymatic browning during the extraction process will reduce the phenolic acid content of the resulting extract.

DNA Repair Enzymes

The composition may also contain one or more DNA repair enzymes. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-Guanine base damage.

Another type of DNA repair enzyme that may be used is one that is known to be effective in repairing 06-methyl guanine base damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of Micrococcus lysate (an end product of the controlled lysis of various species of micrococcus), lecithin, and water. Photosomes® comprise a mixture of plankton extract (which is the extract of marine biomass which includes one or more of the following organisms: thalassoplankton, green micro-algae, diatoms, greenish-blue and nitrogen-fixing seaweed), water, and lecithin.

Other suitable DNA repair enzymes include Endonuclease V, which may be produced by the denV gene of the bacteriophage T4. Also suitable are T4 endonuclease; O⁶-methylguanine-DNA methyltransferases; photolyases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; topoisomerase; O⁶ benzyl guanine; DNA glycosylases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as O⁶-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch exision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma pigmentosum group C-complementing protein (XPC); RAD23 (*S. cerevisiae*) homolog (RAD23B);

caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog ((REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

The compositions of the invention may contain one or more DNA repair enzymes.

Humectants

The composition may contain one or more humectants. If present, they may range from about 0.01 to 75%, preferably from about 0.5 to 70%, more preferably from about 0.5 to 40%. Examples of suitable humectants include glycols, sugars, and the like. Suitable glycols are in monomeric or polymeric form and include polyethylene and polypropylene glycols such as PEG 4-10, which are polyethylene glycols having from 4 to 10 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

Sunscreens

It may also be desirable to include one or more sunscreens in the compositions of the invention. Such sunscreens include chemical UVA or UVB sunscreens or physical sunscreens in the particulate form. Inclusion of sunscreens in the compositions containing the whitening active ingredient will provide additional protection to skin during daylight hours and promote the effectiveness of the whitening active ingredient on the skin. If present, the sunscreens may range from about 0.1 to 50%, preferably from about 0.5 to 40%, more preferably from about 1 to 35%.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds of the formula:

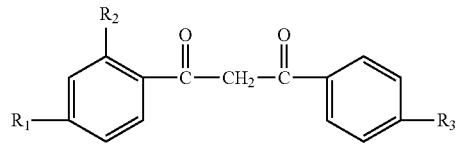

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercially available from Givaudan-Roure under the trademark Parsol® 1789, and Merck & Co. under the tradename Eusolex® 9020.

Other types of UVA sunscreens include dicamphor sulfonic acid derivatives, such as ecamsule, a sunscreen sold under the trade name Mexoryl®, which is terephthalylidene dicamphor sulfonic acid, having the formula:

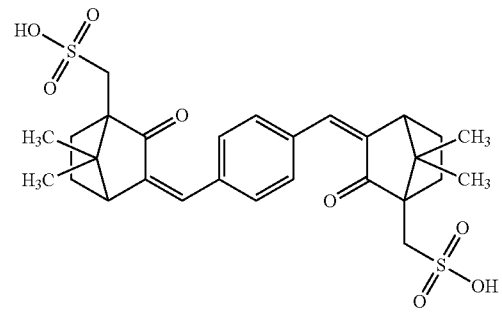 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 10% by weight of the total composition of octocrylene. Suitable amounts range from about 0.001-10% by weight. Octocrylene may be purchased from BASF under the tradename Uvinul® N-539.

Other suitable sunscreens include benzylidene camphor derivatives as set forth in U.S. Pat. No. 3,781,417, which is hereby incorporated by reference in its entirety. Such benzylidene camphor derivatives have the general formula:

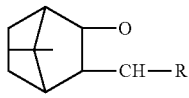

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

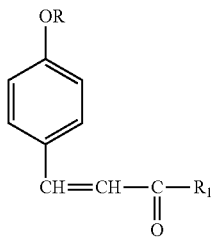

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol® MCX, or BASF under the tradename Uvinul® MC 80.

Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

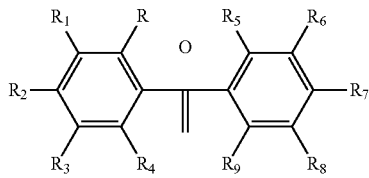

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

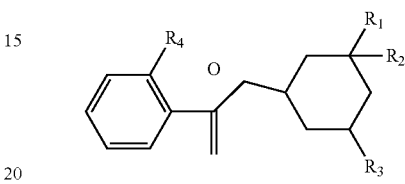

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the trademark Eusolex® HMS and menthyl anthranilate is commercially available from Haarmann & Reimer under the trademark Heliopan®. If present, the Homosalate should be found at no more than about 15% by weight of the total composition.

Various amino benzoic acid derivatives are suitable UVB absorbers including those having the general formula:

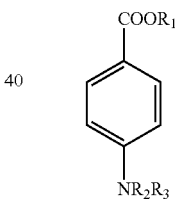

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have certain SPF (sun protective factor) values ranging from about 1-50, preferably about 2-45, most preferably about 5-30. Calculation of SPF values is well known in the art.

Surfactants

It may be desirable for the composition to contain one more surfactants, especially if in the emulsion form. However, such surfactants may be used if the compositions are solutions, suspensions, or anhydrous also, and will assist in dispersing ingredients that have polarity, for example pigments. Such surfactants may be silicone or organic based. The surfactants will also aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

1. Organic Nonionic Surfactants

The composition may comprise one or more nonionic organic surfactants. Suitable nonionic surfactants include alkoxylated alcohols or ethers, formed by the reaction of an alcohol with an alkylene oxide, usually ethylene or propylene oxide. Suitable alcohols include mono-, di-, or polyhydric short chain ($C_{1-6}$) alcohols; aromatic or aliphatic saturated or unsaturated fatty ($C_{12-40}$) alcohols, of cholesterol; and so on.

In one embodiment the alcohol is cholesterol, or an aromatic or aliphatic saturated or unsaturated fatty alcohol which may have from 6 to 40, preferably from about 10 to 30, more preferably from about 12 to 22 carbon atoms. Examples include oleyl alcohol, cetearyl alcohol, cetyl alcohol, stearyl alcohol, isostearyl alcohol, behenyl alcohol, and the like. Examples of such ingredients include Oleth 2-100; Steareth 2-100; Beheneth 5-30; Ceteareth 2-100; Ceteth 2-100; Choleth 2-100 wherein the number range means the number of repeating ethylene oxide units, e.g. Ceteth 2-100 means Ceteth where the number of repeating ethylene oxide units ranges from 2 to 100. Derivatives of alkoxylated alcohols are also suitable, such as phosphoric acid esters thereof.

Some preferred organic nonionic surfactants include Oleth-3, Oleth-5, Oleth-3 phosphate, Choleth-24; Ceteth-24; and so on.

Also suitable are alkoxylated alcohols formed with mono-, di-, or polyhydric short chain alcohols, for example those having from about 1 to 6 carbon atoms. Examples include glucose, glycerin, or alkylated derivatives thereof. Examples include glycereth 2-100; gluceth 2-100; methyl gluceth 2-100 and so on. More preferred are methyl gluceth-20; glycereth-26 and the like.

Other types of alkoxylated alcohols are suitable surfactants, including ethylene oxide polymers having varying numbers of repeating EO groups, generally referred to as PEG 12 to 200. More preferred are PEG-75, which is may be purchased from Dow Chemical under the trade name Carbowax PEG-3350.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, sorbitan oleate, sorbitan sesquioleate, sorbitan palmitate, sorbitan sesquiisostearate, sorbitan stearate, and so on.

2. Silicone or Silane Surfactants

Also suitable are various types of silicone or silane-based surfactants. Examples include organosiloxanes substituted with ethylene oxide or propylene oxide groups such as PEG dimethicones which are dimethicones substituted with polyethylene glycols including those having the INCI names PEG-1 dimethicone; PEG-4 dimethicone; PEG-8 dimethicone; PEG-12 dimethicone; PEG-20 dimethicone; and so on.

Also suitable are silanes substituted with ethoxy groups or propoxy groups or both, such as various types of PEG methyl ether silanes such as bis-PEG-18 methyl ether dimethyl silane; and so on.

Further examples of silicone based surfactants include those having the generic names dimethicone copolyol; cetyl dimethicone copolyol; and so on.

Botanical Extracts

It may be desirable to incorporate one more additional botanical extracts into the composition. If present suggested ranges are from about 0.0001 to 20%, preferably from about 0.0005 to 15%, more preferably from about 0.001 to 10%. Suitable botanical extracts include extracts from plants (herbs, roots, flowers, fruits, seeds) such as flowers, fruits, vegetables, and so on, including yeast ferment extract, *Padina Pavonica* extract, *Thermus Thermophilis* ferment extract, *Camelina Sativa* seed oil, *Boswellia Serrata* extract, olive extract, *Acacia Dealbata* extract, *Acer Saccharinum* (sugar maple), *Acidopholus, Acorus, Aesculus, Agaricus, Agave, Agrimonia*, algae, aloe, citrus, *Brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum, Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea, Kola Acuminata*, and mixtures thereof. If desired such botanical extracts may be fermented to increase potency or activity. Fermentation may be accomplished by standard fermentation techniques using bacteria or yeast.

Biological Materials

Also suitable are various types of biological materials such as those derived from cells, fermented materials, and so on. If present such materials may range from about 0.001 to 30%, preferably from about 0.005 to 25%, more preferably from about 0.01 to 20%. Examples include fragments of cellular RNA or DNA, probiotic microorganisms, or ferments of microorganisms and organic materials from plants such as leaves, seeds, extracts, flowers, etc. Particularly preferred are RNA fragments.

Aqueous Phase Structuring Agents

In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below.

1. Polysaccharides

Polysaccharides may be suitable aqueous phase thickening agents. Examples of such polysaccharides include naturally derived materials such as agar, agarose, alicaligenes polysaccharides, algin, alginic acid, acacia gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

2. Acrylate Polymers

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymers of A, B, and C monomers wherein A and B are as defined above, and C has the general formula:

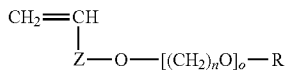

wherein Z is $-(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

Also suitable are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

3. Alkylene Glycols

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

Oils

In the event the compositions of the invention are in emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C. If present, such oils may range from about 0.01 to 85%, preferably from about 0.05 to 80%, more preferably from about 0.1 to 50%.

1. Volatile Oils

Suitable volatile oils generally have a viscosity ranging from about 0.5 to 5 centistokes 25° C. and include linear silicones, cyclic silicones, paraffinic hydrocarbons, or mixtures thereof.

(a). Volatile Silicones

Cyclic silicones are one type of volatile silicone that may be used in the composition.

Such silicones have the general formula:

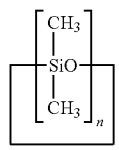

where n=3-6, preferably 4, 5, or 6.

Also suitable are linear volatile silicones, for example, those having the general formula:

$(CH_3)_3Si—O—[Si(CH_3)_2—O]_n—Si(CH_3)_3$ where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone having the general formula:

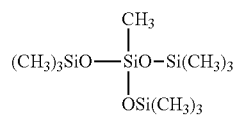

Methyl trimethicone may be purchased from Shin-Etsu Silicones under the tradename TMF-1.5, having a viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof.

(i) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisostearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(d). Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

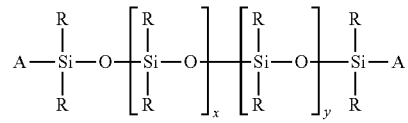

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

Vitamins and Antioxidants

It may be desirable to incorporate one or more vitamins or antioxidants in the compositions. If present, suggested ranges are from about 0.001 to 20%, preferably from about 0.005 to 15%, more preferably from about 0.010 to 10%. Preferably such vitamins, vitamin derivatives and/or antioxidants are operable to scavenge free radicals in the form of singlet oxygen. Such vitamins may include tocopherol or its derivatives such as tocopherol acetate, tocopherol ferulate; ascorbic acid or its derivatives such as ascorbyl palmitate, magnesium ascorbyl phosphate; Vitamin A or its derivatives such as retinyl palmitate; or vitamins D, K, B, or derivatives thereof.

Preferred Compositions

Preferred compositions are in the aqueous solution or emulsion form and contain at least one Pro-Resolving Activator and/or at least one Inflammatory Metabolite Inhibitor or both in the amounts set forth herein.

Further embodiments of the composition include but are not limited to the following with the percentage ranges of such ingredients as set forth above.
A composition comprising:
A Pro-Resolving Activator,
An Inflammatory Metabolite Inhibitor,
A DNA repair enzyme.
Another embodiment is a composition comprising:
A Pro-Resolving Activator,
An autophagy activator,
And optionally an Inflammatory Metabolite Inhibitor.
Another embodiment is a composition comprising:
A Pro-Resolving Activator,
A proteasome activator,
And optionally an Inflammatory Metabolite Inhibitor.
Another embodiment is a composition comprising:
A Pro-Resolving Activator,
An Inflammatory Metabolite Inhibitor,
In the form of an aqueous solution or suspension.

The invention will be further described in connection with the following examples which are set forth for the purposes of illustration only.

Example 1

Ingredients were tested to assess the ability to promote Pro-Resolution Pathway Stimulators in human neutrophils. The following Inflammatory Metabolites were measured: PGE2 and LTB4. The Inflammatory Metabolite Marker, 5-HETE, was measured. Also measured were the Pro-Resolving Lipid Mediator Markers 15-HETE, 12-HETE, 14-HDOHE, 18-HEPE, and 17-HDOHE. PGE2, LTB4, and 5-HETE are indicators of inflammation. Increases in cellular secretion of PGE2, LTB4, or 5-HETE are seen in response to inflammation precipitating conditions. Active ingredients that cause a reduction in cellular concentration of PGE2, LTB4, or 5-HETE are anti-inflammatory in nature. Cellular secretion of Pro-Resolving Lipid Mediators occurs in the inflammation resolution phase. Active ingredients that stimulate cellular secretion of Pro-Resolving Lipid Mediators (as measured by measuring Pro-Resolving Lipid Mediator Markers) help to promote resolution of inflammation.

The following active ingredients were tested: salicylic acid, resveratrol salicylate, resveratrol, *Perilla ocymoides* seed oil, *Camellia japonica* extract, *Poria cocos* extract, *Aleurites moluccana* (Kukui) seed oil, *Camelina sativa* seed oil, *Dongbaek* (Tsubaki) oil, Bifida ferment lysate, *Lactobacillus*, and *Dhotela* oil.

Concentrations of each of the above active ingredients appropriate for test purposes was determined by doing serial dilutions of each active in triplicate at eight different concentrations and assessing cytotoxic concentrations on neutrophils using the Almar Blue Cell Viability Assay protocol, Life Technologies, according to manufacturer's instructions.

Neutrophils were plated at a concentration of $5 \times 10^5$ cells (100 µl) in a 96 well plate. The first row of the plate was left empty for background measurement and wells containing medium alone were used as an untreated control. After 24 hours incubation at 37° C. test samples were added to each well in triplicate in the amounts determined as set forth in Figure I. The plate was incubated overnight at 37° C. The next morning the treatment medium was removed and the wells washed with 200 µl phosphate buffered saline ("PBS") followed by 100 µl of 10% Almar Blue solution added. The plate was incubated at 37° C. for 24 hours. The fluorescence was measured at 560 nm/EM 590 nm) at 24 hours using a Spectra Max Gemini reader. The appropriate concentrations for further testing were selected based upon observed cytotoxicity, that is, concentration ranges below those which were demonstrated to be cytotoxic to cells. Non-toxic concentrations were defined as those that induced 10% or less cytotoxicity. The results of the cytotoxicity study showing appropriate test concentrations for each active are set forth in FIGS. 1A, 1B, and 1C.

Neutrophils were plated at a concentration of $5 \times 10^5$ cells (100 µl) in a 96 well plate as above, and pre-treated with active at the concentration ranges determined in cytotoxicity testing as set forth in Figure I for 24 hours. Then, the inflammatory response was initiated by adding an inflammation precipitating ingredient, in particular PMA/A21387 which is a mixture of 5-(methylamino)-2-({(2R,3R,6S,8S,9R,11R)-3,9,11-trimethyl-8-[(1S)-1-methyl-2-oxo-2-(1H-pyrrol-2-yl)ethyl]-1,7-dioxaspiro[5.5]undec-2-yl}methyl)-1,3-benzoxazole-4-carboxylic acid and PMA (phorbol myristate acetate), at a concentration of 0.05 µm and 1 µm respectively to each well. After one hour the supernatants were collected and stored at −80° C. until assayed.

Cell supernatants were assayed for Inflammatory Metabolites (PGE2, LBT4), Inflammatory Metabolite Markers (5-HETE), and Pro-Resolving Lipid Mediator Markers 15-HETE, 12-HETE, 14-HDOHE, 18-HEPE, and 17-HDOHE. More specifically, analysis was performed by extraction using an Oasis HLB 96-well plate (Waters) according to manufacturer's directions.

Then LC-Ms/MS (liquid chromatography tandem mass spectrometry) analysis was performed on extracted samples using the Agilent 1290 Infinity UHPLC according to manufacturer instructions.

The results obtained when measuring the Inflammatory Metabolites or Inflammatory Metabolite Markers and Pro-Resolving Lipid Mediator Markers were expressed in % change compared to the numeric value obtained for the control (PMA/A23187 treated cells). The results are set forth in FIG. 2. Active ingredients that are Inflammatory Metabolite Inhibitors can be ascertained by measuring Inflammatory Metabolites or Inflammatory Metabolite Markers, which values will decrease when cells are treated with actives that have activity in inhibiting Inflammatory Metabolites secreted from cells in response to inflammation precipitating conditions. This is shown by a negative number when the control cells treated with active are compared with cells treated with PMA/23187, the inflammation precipitating ingredient. Suitable Inflammatory Metabolite Inhibitors can be selected based on upon a net negative number or expressed as a percentage decrease when the cellular concentrations of PGE2, LTB4, and 5-HETE are measured in cells exposed to an inflammation precipitating condition either before or after treatment with an active. Suitable Pro-Resolving Activators are ingredients that show an increase in cellular concentration of Pro-Resolving Lipid Mediator Markers 15-HETE, 12-HETE, 14-HDOHE, 18-HEPE, and 17-HDOHE alone or in combination, when cells exposed to an inflammation precipitating condition either before or after exposure to the active.

The results show that when cells exposed to inflammation precipitating conditions were exposed to salicylic acid at concentrations ranging from 0.33 to 33 μg/ml the cellular concentration of Inflammatory Metabolites and Inflammatory Metabolite Markers showed a net decrease (−29, −58, and −46) of 29%, 58% and 46% respectively when compared to control cells subjected only to the inflammation precipitating condition. More specifically, at a concentration of 33 μg/ml the cellular concentration of Inflammatory Metabolites PGE2 and LTB4 decreased 19% and 17% respectively; at a concentration of 3.3 μg/ml the concentration of PGE2 and LTB4 decreased 28% and 12% respectively, and at 0.33 μg/ml the concentration of PGE2 and LTB4 decreased 19% and 1% respectively. The cellular concentration of 5-HETE, an Inflammatory Metabolite Marker, decreased 27%, 20%, and 15% when exposed to salicylic acid at concentrations of 33, 3.3 and 0.33 μg/ml respectively. Accordingly salicylic acid is a suitable Inflammatory Metabolite Inhibitor.

However, cells exposed to salicylic acid at the concentrations tested showed that it was not particularly effective as a Pro-Resolving Activator, showing, in the aggregate, a decrease in cellular concentration of Pro-Resolving Lipid Mediators and/or Pro-Resolving Lipid Mediator Markers. For example, at a concentration of 33 μg/ml cells treated with salicylic acid showed a decrease in cellular concentration of the Pro-Resolving Lipid Mediator Marker 15-HETE, and the cellular concentration of all the Pro-Resolving Lipid Mediator Markers in the aggregate decreased when compared to control cells at concentrations of 33 and 3.3 μg/ml. Thus, cells exposed to salicylic acid and an inflammation precipitating condition do not show an increase in cellular concentration of Pro-Resolving Lipid Mediators and/or Pro-Resolving Lipid Mediator Markers at higher concentrations ranging from 3.3 to 33 μg/ml. However at the lower concentration of 0.33 ug/ml there is a small increase in cellular concentration of Pro-Resolving Lipid Mediators. While salicylic acid may be an effective Inflammatory Metabolite Inhibitor, it is not effective as a Pro-Resolving Activator and exhibits a positive % change over control cells only at the very low concentration of 0.33 μg/ml.

Cells treated with resveratrol at concentrations of 10 ug/ml, 1 ug/ml and 0.1 ug/ml showed significant inhibition of Inflammatory Metabolites with cellular decrease in Inflammatory Metabolite Inhibitors and Inflammatory Metabolite Inhibitor Markers showing a (−106, −59, and −45) 106%, 59% and 45% decrease when compared to control cells exposed to the inflammation precipitating condition. However, as with salicylic acid, cellular concentrations of Pro-Resolving Lipid Mediator Markers, in the aggregate, were decreased after exposure to resveratrol. Specifically when cells were exposed to resveratrol concentrations of 10, 1 and 0.1 ug/ml the Pro-Resolving Lipid Mediator Markers decreased when compared to control (−10, −16, and −27). Thus resveratrol is not a good Pro-Resolving Activator.

Resveratrol salicylate is both an Inflammatory Metabolite Inhibitor and a Pro-Resolving Activator. Results show that when cells were exposed to concentrations of resveratrol salicylate ranging from 43, 4.3, and 0.43 ug/ml the cellular concentration of Inflammatory Metabolites and Inflammation Metabolite Markers decreased in the aggregate (−257, −163, and −87) thus showing activity as an Inflammatory Metabolite Inhibitor that was 257%, 163% and 87% respectively, better than control. Similarly, cells treated with resveratrol salicylate showed an increase cellular concentration of Pro-Resolving Lipid Mediator Markers, in the aggregate, of 37%, 4%, at concentration ranges of 4.3 to 43 ug/ml with the lowest concentration range of 0.43 ug/ml not being as effective. However, resveratrol salicylate is both an Inflammatory Metabolite Inhibitor and a Pro-Resolving Activator.

Most effective as both an Inflammatory Metabolite Inhibitor and a Pro-Resolving Activator are inactivated cultures of *Bifidobacterium*. Testing of Bifida ferment lysate showed a 107% decrease in cellular concentration of Inflammatory Metabolites and Inflammatory Metabolite Inhibitors and a 546% increase in cellular concentration of Pro-Resolving Activators when compared with control. Thus Bifida ferment lysate is excellent Pro-Resolution Pathway Stimulator.

Example 2

A formula with Pro-Resolution Pathway Simulator activity was prepared as follows:

| Ingredient | % by weight |
|---|---|
| Caprylic/capric triglyceride | QS100 |
| Squalane | 9.90 |
| *Aleurites Moluccana* (Kukui) seed oil | 3.50 |
| *Salvia hispanica* seed extract/tocopherol | 1.00 |
| Bisabolol | 1.00 |
| *Prunus armeniaca* (Apricot) Kernel Oil | 1.00 |
| Caprylic/capric triglyceride/*Salicornia herbacea* extract | 0.50 |
| Tocopherol acetate | 0.20 |
| Linoleic acid | 0.20 |
| Cholesterol | 0.20 |
| *Camelina sativa* seed oil | 0.10 |
| Tetrahexyldecyl ascorbate | 0.10 |
| BHT | 0.09 |
| *Anthemis nobilis* (Chamomile) extract | 0.08 |
| *Coffea arabica* (coffee) seed extract | 0.05 |
| *Magnolia officinalis* bark extract | 0.05 |
| *Vaccinium myrtillus* seed oil | 0.02 |
| *Garcinia Mangostana* peel extract | 0.01 |

The composition was prepared by combining the ingredients and mixing well.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A method for formulating a topical composition comprising:
   (a) identifying an Inflammatory Metabolite Inhibitor by exposing cells treated and untreated with a test ingredient to an inflammation precipitating condition, measuring the amount of Inflammatory Metabolites or Inflammatory Metabolite Markers released and selecting the test ingredient that causes a decrease in cellular release of Inflammatory Metabolites or Inflammatory Metabolite Markers when compared to untreated cells wherein:
      (i) the Inflammatory Metabolites are one or more of cyclic endoperoxidases derived from arachidonic acid; Prostacyclin 12 (PG12): Prostaglandin E2 (PGE2); Prostaglandin F2 alpha (PGF2 alpha); Prostaglandin A2 (PGA2); Prostaglandin D2 (PGD2); Leukotriene A4 (LTA4): Leukotriene B4 (LTB4); Leukotriene C4 (LTC4); Leukotriene D4 (LTD4); Platelet Activating Factor (PAF); Interleukin-1 alpha (IL-1 alpha); Interleukin-1 beta (IL-1 beta); Interleukin-6 (IL-6); Interleukin-8 (IL-8); Tumor necrosis factor alpha (TNF alpha); and monocyte chemotactice protein (MCP-1); and
      (ii) the Inflammatory Metabolite Markers are one or more of 5-hydroxyeicosatetraenoic acid (5-HETE); 5-hydroxyperoxyeicosatetraenoic acid (H-HPETE); Leukotriene E4 (LTE4); Prostaglandin G2 (PGG2); Prostaglandin H2 (PGH2); endoperoxide precursors of PGE2; Prostaglandin J2 (PGJ2); Prostaglandin 12 (PG12); and 6-keto Prostaglandin F1 alpha;
   (b) identifying a Pro-Resolving Activator by exposing cells treated and untreated with a test ingredient to an inflammation precipitating condition, measuring the amount of Pro-Resolving Activators released and selecting the test ingredient that shows an increase in cellular release of Pro-Resolving Activators when compared to the untreated cells wherein the Pro-Resolving Activator is one or more of:
      (i) a Pro-Resolving Lipid Mediator which is one or more of Resolvin; Protectin; Lipoxin; or Maresin; or
      (ii) a Pro-Resolving Lipid Mediator Marker which is one or more of cyclooxygenase (COX); lipoxygenase (LOX); cytochrome epoxygenase (CYPe); Cyctochrome hydrolase (CYP); 15-hydroxyeicosapentaenoic acid (15-HETE); 12-hydroxyeicosapentaenoic acid (12-HETE); 14-hydroxydocosahexaenoic acid (14-HDOHE); 18-hydroxyeicosapentaenoic acid (18-HEPE); and 17-hydroxydocosahexaenoic acid (17HDOHE); and
   (c) formulating the test ingredient(s) selected in (a) and (b) into a topical composition.

2. The method of claim 1 wherein the cells in (a) or (b) are exposed to an inflammation precipitating condition before they are exposed to the test ingredient.

3. The method of claim 1 wherein the cells in (a) or (b) are exposed to an inflammation precipitating condition after they are exposed to the test ingredient.

4. The method of claim 1 wherein the cells are keratinocytes or fibroblasts.

5. The method of claim 1 wherein the topical composition is for application to skin, hair, or nails and the selected ingredient is both an Inflammatory Metabolite Inhibitor and a Pro-Resolving Activator.

6. The method of claim 1 wherein the test ingredient that is selected shows both:
   (i) a decrease in cellular concentration of Inflammatory Metabolites or Inflammatory Metabolite Markers individually or in combination; and
   (ii) an increase in cellular concentration of Pro-Resolving Lipid Mediators or Pro-Resolving Lipid Mediator Markers individually or in combination.

7. The method of claim 6 wherein the test ingredient is present from 0.001 to 15% by weight of the total topical composition.

8. The method of claim 6 wherein the topical composition is in the form of an emulsion, solution, dispersion, gel, or anhydrous composition.

9. The method of claim 8 wherein the topical composition is in the form of an emulsion.

10. The method of claim 9 wherein the topical composition additionally contains one or more of an autophagy activator, a proteasome activator, a CLOCK or PER1 gene activator, or a DNA repair enzyme.

11. The method of claim 9 wherein the topical composition is in the form of an oil in water emulsion comprising 5 to 90% water and 5 to 75% oil.

12. The method of claim 11 wherein the topical composition contains inactivated cultures of *Bifidobacterium*.

13. The method of claim 12 wherein the inactivated cultures of *Bifidobacterium* are Bifida lysate, Bifida ferment lysate, Bifida filtrate.

14. The method of claim 12 wherein the inactivated cultures of *Bifidobacterium* are from *Bifidobacterium longum*.

15. The method of claim 11 wherein the topical composition comprises a probiotic microorganism.

16. A topical composition made according to the method of claim 1.

* * * * *